United States Patent
Lubrecht

(10) Patent No.: US 6,200,627 B1
(45) Date of Patent: Mar. 13, 2001

(54) LOW SILICONE GLASS PREFILLABLE SYRINGE

(75) Inventor: Thea E. Lubrecht, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/265,677

(22) Filed: Mar. 10, 1999

Related U.S. Application Data

(60) Provisional application No. 60/078,266, filed on Mar. 17, 1998.

(51) Int. Cl.[7] .............................. B05D 3/06; A61M 5/315
(52) U.S. Cl. ...................... 427/2.28; 427/2.3; 427/242; 427/487; 604/15; 604/218
(58) Field of Search .......................... 427/228, 2.3, 487, 427/515, 503, 242, 314; 604/15, 218, 220, 222

(56) References Cited

U.S. PATENT DOCUMENTS

| | | | |
|---|---|---|---|
| 3,656,480 | * 4/1972 | Rubricius | 128/218 P |
| 3,948,864 | * 4/1976 | Bargain et al. | 260/78.3 R |
| 4,064,286 | * 12/1977 | Hahn | 427/44 |
| 4,806,430 | 2/1989 | Spielvogel et al. . | |
| 4,822,632 | * 4/1989 | Williams et al. | 427/34 |
| 4,872,572 | 10/1989 | Schrooten . | |
| 5,000,994 | 3/1991 | Romberg et al. . | |
| 5,061,252 | 10/1991 | Dragosits . | |
| 5,456,940 | 10/1995 | Funderburk . | |
| 5,607,400 | * 3/1997 | Thibault et al. | 604/230 |
| 5,807,605 | * 9/1998 | Tingey et al. | 427/8 |

FOREIGN PATENT DOCUMENTS

| | | |
|---|---|---|
| 0092383A2 | 4/1983 | (EP) . |
| 0111724A2 | 11/1983 | (EP) . |
| 0570978A1 | 5/1993 | (EP) . |
| 0627474A1 | 4/1994 | (EP) . |
| 0651005A1 | 10/1994 | (EP) . |

* cited by examiner

Primary Examiner—Shrive Beck
Assistant Examiner—Jennifer Kolb
(74) Attorney, Agent, or Firm—Allen W. Wark

(57) ABSTRACT

A method for lubricating a sealing member in a drug delivery device includes the steps of washing and rinsing the sealing members in hot deionized water following by drying the sealing members. The dried sealing members are tumbled with polymeric silicone and then irradiated at a target dose between 2.5 and 4.0 Mrads. The irradiated sealing members are then utilized in a variety of drug delivery devices including syringes, pre-filled syringes, drug cartridges, and needleless injector ampules.

9 Claims, 2 Drawing Sheets

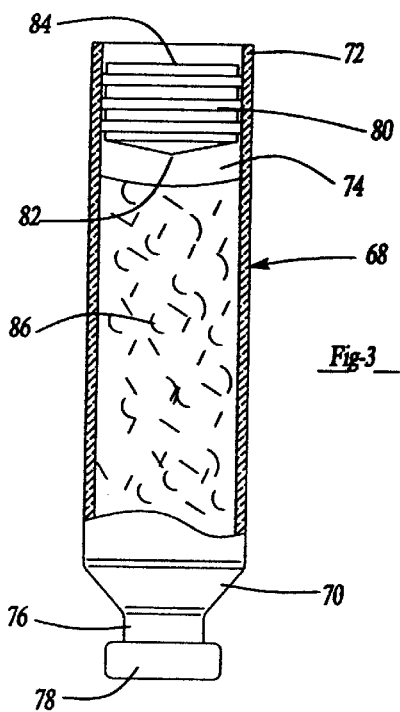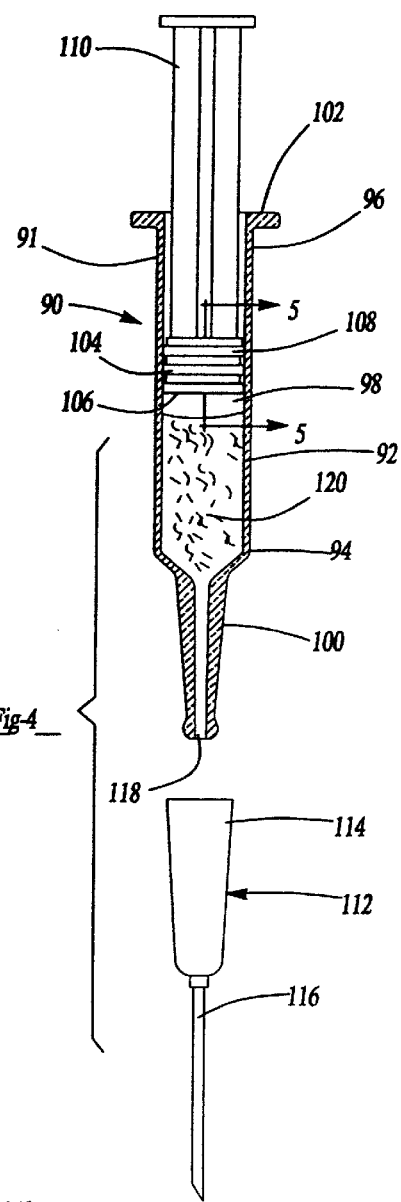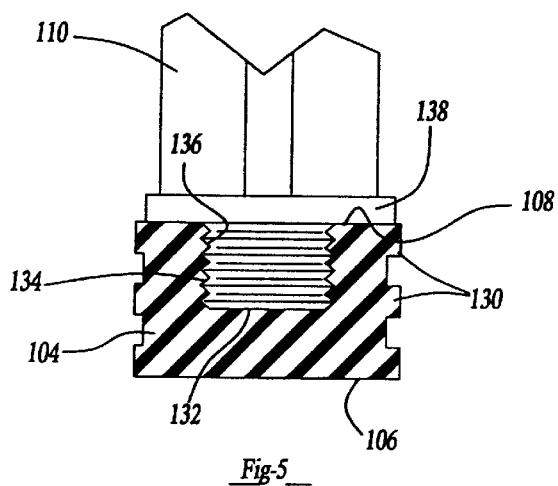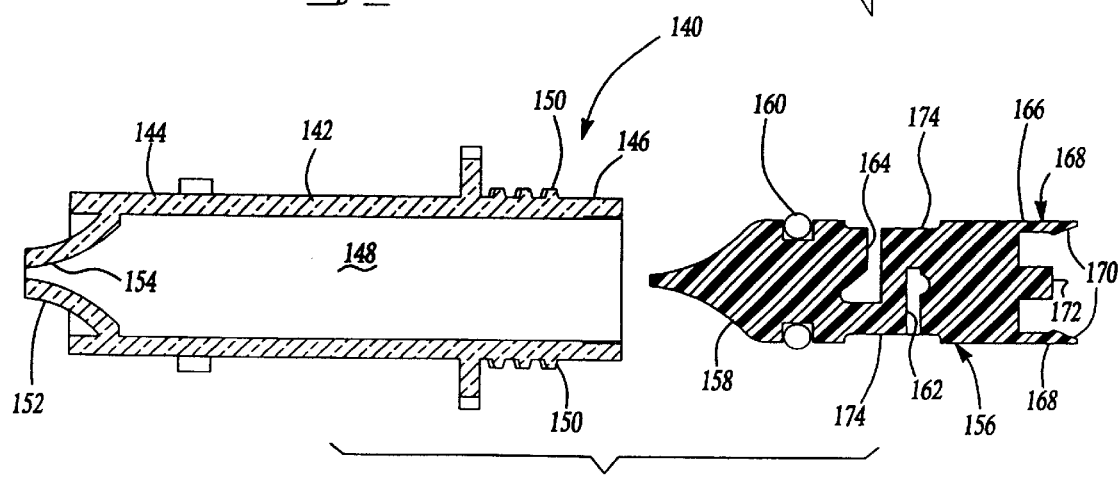

LOW SILICONE GLASS PREFILLABLE SYRINGE

This Application claim benefit to Provisional Application 60/078,266 filed Mar. 17, 1998.

BACKGROUND OF THE INVENTION

This invention relates generally to a method of providing lubrication in a drug delivery system and, more particularly, to a method of lubricating a sealing member of a drug delivery system with a polymeric silicone.

Many drug delivery systems, like syringes, pre-filled syringes, drug cartridges and needleless injectors include an interior chamber for receiving a medicament and a sealing member. The sealing member is usually slidable within the interior chamber and in a fluid-tight relationship with the walls forming the interior chamber.

The sealing member can take many forms, with two conventional forms being a stopper and an O-ring. The sealing members are often made of rubber or elastomeric materials. The interior chamber of many drug delivery systems is made of glass. The fluid-tight relationship between the sealing member and the wall forming the interior chamber provides a large resistance to movement of the sealing member within the interior chamber. Typically, this resistance has been reduced by pre-treating the walls of the interior chamber and the sealing member with a lubricating solution such as silicone. In the typical coating method, the sealing member is agitated with a solution of the silicone and then the sealing member is removed from the silicone solution and placed in the interior chamber of a drug delivery system. Typically, the walls of the interior chamber have also been pre-treated with a silicone solution.

There are several disadvantages with the typical lubricating method. The first disadvantage is that it requires coating both the sealing member and the interior chamber with a lubricating solution. A second disadvantage is that the lubricant typically is only loosely adhered to the sealing member or the interior chamber. This loose adherence permits the lubricating solution, for instance silicone, to be deposited into a medicament loaded in the drug delivery system. In some instances, spheres of silicone have been found suspended within the medicament solution.

Therefore, a drug delivery system that prevents the lubricant from becoming deposited in the medicament is desirable. This invention includes lubricating only the sealing member and prevents the lubricant from accumulating in the medicament.

SUMMARY OF THE INVENTION

In general terms, this invention includes a method for coating a sealing member of a drug delivery system with polymeric silicone to provide a lubrication layer on the sealing member. The polymeric silicone in the lubricating layer is crosslinked by radiation and adheres to the sealing member.

The method of this invention includes the steps of coating a sealing member with a polymeric silicone having a plurality of polymer molecules and then exposing the coated sealing member to irradiation. Cobalt radiation is most preferred, at a target dose between 2.5 to 4.0 Mrads. Irradiating the coated sealing member forms crosslinks between the molecules of the polymeric silicone and causes the crosslinked molecules to adhere to the sealing member, thus forming a lubricating layer. The preferred embodiment of this invention includes using polymeric silicone having a relatively high viscosity when forming the lubricating layer.

The inventive method prevents the polymeric silicone from being deposited into the medicament. The method of the invention further permits the manufacture of a drug delivery system wherein only one of the sealing member or the interior chamber is lubricated.

These and other features and advantages of this invention will become more apparent to those skilled in the art from the following detailed description of the presently preferred embodiment. The drawings that accompany the detailed description can be briefly described as follows.

BRIEF DESCRIPTION OF THE DRAWINGS

FIG. 3 is a side cross-sectional view of a drug delivery cartridge.

FIG. 4 is an exploded side view of a syringe and a needle cannula.

FIG. 5 is a cross-sectional side view of a stopper and a plunger.

FIG. 6 is an exploded side view of a medicament cartridge that can be used with needleless injector.

DETAILED DESCRIPTION OF THE PREFERRED EMBODIMENT

Figure 1:
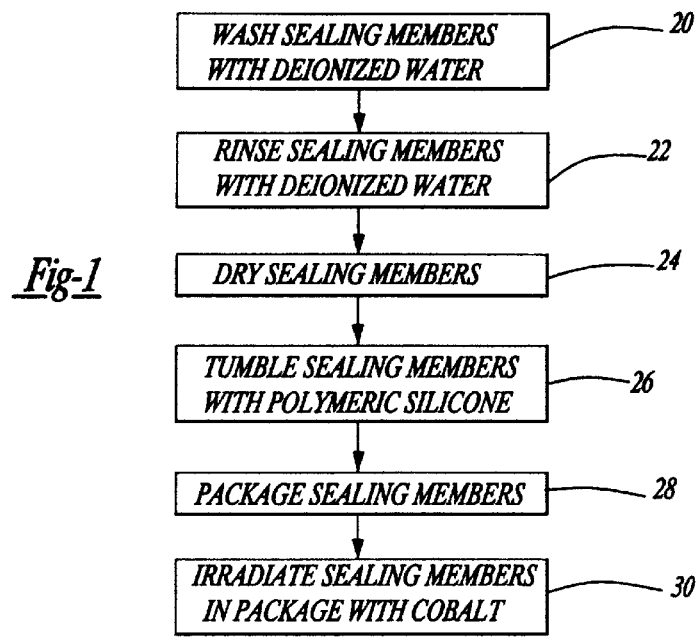
FIG. 1 is a flowchart illustrating the steps of lubricating a sealing member according to the method of this invention.

A flow chart of the method of this invention is provided at 10 in FIG. 1. In step 20, the sealing members are washed. Preferably the sealing members are washed with hot deionized water. Most preferably, the sealing members are washed in deionized water at a temperature between 154 and 181° F. for 1.5 minutes.

In step 22 the sealing members are rinsed. Preferably, the sealing members are rinsed in deionized water. Most preferably, the sealing members are rinsed in deionized water at a temperature between 154 and 181° F. for 7.5 minutes.

In step 24 the sealing members are dried. Most preferably, the sealing members are dried for 30 minutes at 200° F.

In step 26, the sealing members are tumbled with polymeric silicone to coat the sealing members. Most preferably, the sealing members are tumbled with polymeric silicone for 60 minutes to coat the sealing members. A conventional tumbling device can be used.

In step 28, the coated sealing members are packaged in a container. Most preferably, the coated sealing members are packaged and sealed in the container. In step 30, the packaged and coated sealing members are irradiated. Most preferably, the packaged and coated sealing members are irradiated with Cobalt at a target dose of 2.5 to 4.0 Mrads. The radiation provides cross linking between the silicone molecules and adheres the silicone to the stopper. Thus, steps 20 through 30 produce a lubricated, sterile, sealing member.

Figure 2:
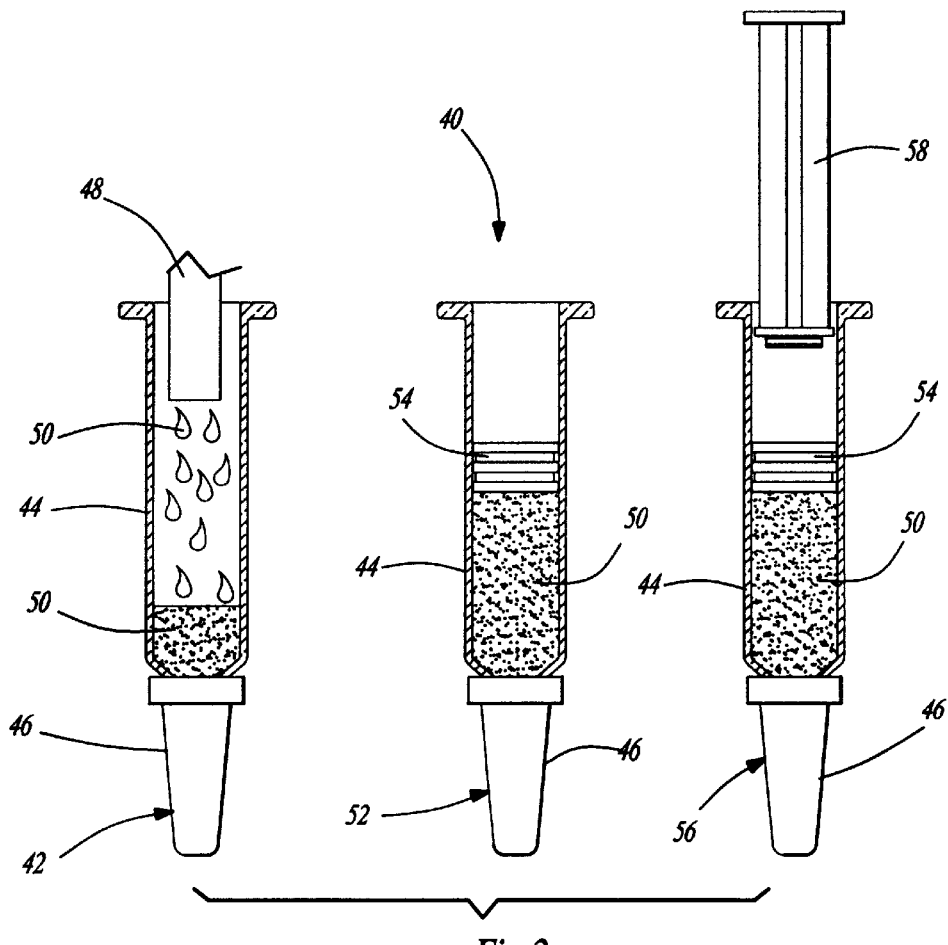
FIG. 2 is a schematic illustration of the processing steps of manufacturing a prefilled syringe using a lubricated sealing member designed according to the present invention.

A schematic diagram of the processing steps of manufacturing a prefilled syringe using a lubricated sealing member designed according to the present invention is generally indicated at 40 in FIG. 2. As shown at 42, a glass syringe 44 having a needle shield 46 receives a fill tube 48. The fill tube 48 dispenses a medicament 50 into the syringe 44 to fill the syringe 44. In the stage illustrated at 52, a coated, lubricated, and irradiated sealing member 54, made according to the method described above, is inserted into the syringe 44 in a fluid-tight relationship over the medicament 50. At 56, a plunger 58 is inserted into the sealing member 54. Put another way, step 42 involves filling the syringe 44 with a medicament 50, step 52 involves placing a lubricated sealing member 54 into the syringe 44, and step 56 involves connecting the plunger 58 and the sealing member 54. Of course, the plunger 58 and the sealing member 54 can be preassembled before step 52 is performed.

The particular polymeric silicone used in the present method is selected in order to be compatible with the particular medicament in the drug delivery system and the material composition of the sealing member. In addition, it is necessary to comply with federal regulations regarding acceptable materials for use in a drug delivery system.

Polymeric silicones that may be used in the method of this invention include: phenyl substitute silicones, vinyl substitute silicones, hydrogen substituted silicones, and others. One especially preferred silicone is known as Med-361, which is a polydimethyl siloxane, produced by Nusil and the most preferred viscosity of Med-361 is 100,000 centistokes. All of these silicones can be used at viscosities between 1,000 and 100,000 centistokes. Acceptable phenyl substituted silicones include: dimethyldiphenylpolysiloxane copolymers; dimethyl, methylphenylpolysiloxane copolymers; polymethylphenylsiloxane; and methylphenyl, dimethylsiloxane copolymers. The higher the phenyl content of the substituted silicone the lower the amount of irradiation induced crosslinking that occurs. The phenyl substituted silicones can be used in a variety of viscosities especially between 12,500 centistokes to 100,000 centistokes.

Vinyl substituted silicones that have been found to be advantageous in the method of this invention include: vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; polydimethylsiloxane, mono vinyl, mono n-butyldimethyl terminated; and vinylphenylmethyl terminated polydimethylsiloxanes. The vinyl substituted silicones also can be made in a variety of viscosities as noted above. Higher vinyl content provides more efficient radiation induced crosslinlding.

The hydrogen substituted silicones that have been found to be advantageous in the method of this invention include: dimethylhydro terminated polydimethylsiloxanes; methylhydro, dimethylpolysiloxanecopolymers; methylhydro terminated methyloctyl siloxane copolymers; and methylhydro, phenylmethyl siloxane copolymers. The hydrogen substituted siloxanes can be used in a variety of viscosities as noted above.

Other substituted silicones that may be used in the method of this invention include: polyfluoroalkylmethyl siloxanes; fluoralkyl, dimethyl siloxanecopolymers; and polymethylalkylsiloxanes.

FIGS. 3 through 6 illustrate example drug delivery assemblies that incorporate a lubricated sealing member made according to this invention. A glass medicament cartridge is shown generally at 66 in FIG. 3. The medicament cartridge 66 comprises a generally cylindrical barrel 68 having a first end 70, a second end 72, and an interior chamber 74. A neck portion 76 is located adjacent the first end 70. A seal 78 surrounds an end of the neck portion 76 and seals the neck portion 76. A lubricated stopper 80, made according to the method described above, is received in a fluid-tight relationship into the interior chamber 74 through the second end 72 of the medicament cartridge 66. The stopper 80 includes a first side 82 and a second side 84. A medicament 86 is located between the first side 82 of the stopper 80 and the seal 78. As will be understood by those skilled in the art, such medicament cartridges 66 are designed to be received in a wide variety of delivery devices (not shown). The delivery devices include a needle cannula for penetrating the seal 78 and a plunger mechanism for moving the stopper 80 from the second end 72 toward the first end 70 to expel the medicament 86 from the interior chamber 74 during an injection.

An exploded side view of a syringe and a needle cannula is generally indicated at 90 in FIG. 4. The syringe 91 includes a cylindrical barrel 92 having a first end 94 and a second end 96 and an interior chamber 98. A neck portion 100 is located adjacent the first end 94. A flange 102 is located adjacent the second end 96. A lubricated stopper 104, formed according to the method of this invention, is received in a fluid-tight relationship into the interior chamber 98. The stopper 104 has a first side 106 and a second side 108. A plunger 110 is received in the second side 108 of the stopper 104. A needle cannula 112 includes a hub 114 and a needle 116. The neck portion 100 includes a fluid channel 118. A medicament 120 is located in the interior chamber 98 between the first side 106 of the stopper 104 and the neck portion 100. The needle cannula 112 is received on the neck portion 100. The fluid channel 118 is in fluid communication with the needle 116.

FIG. 5 is a cross-sectional side view of a portion of the plunger 110 and the lubricated stopper 104. The stopper 104 preferably includes a plurality of ribs 130. An interior space 132 extends from the second side 108 of the stopper 104 into the stopper 104. A set of internal threads 134 lines the interior space 132. A set of external threads 136 are located on the plunger 110 adjacent a plunger base 138. The internal threads 134 are adapted to receive the external threads 136 to secure the plunger 110 to the stopper 104 so the two will move in unison.

An exploded side view of a cartridge for use with a needleless injector is generally shown at 140 in FIG. 6. The cartridge 140 includes a cylindrical barrel 142 having a first end 144, a second end 146, and an interior chamber 148. A luer lock arrangement 150 preferably is located adjacent the second end 146 for securing the cartridge 140 into a needleless injector. A tapered tip 152 is located adjacent the first end 144 and includes a fluid orifice 154. A plunger 156 is slidably received in the interior chamber 148. The plunger 156 includes a tip portion 158 and a lubricated sealing member 160 formed according to the method of this invention, adjacent the tip portion 158. The sealing member 160 is in a fluid-tight relationship with the interior chamber 148 when the plunger 156 is received into the chamber 148. Preferably, the sealing member 160 is an O-ring. The plunger 156 further includes a first cutout 162 and a second cutout 164. A plunger portion 166 includes a series of spaced tabs 168 that facilitate cooperation between an injector driver member (not shown) and the plunger 156. A tab lip 170 is located on each of the spaced tabs 168. A boss 172 is located centrally to the spaced tabs 168. The plunger 156 further includes a pair of slots 174.

As will be understood by those sldlled in the art, the needleless injector cartridge 140 is designed to be utilized with a variety of commercially available injector devices (not shown). The driver mechanism of the device is used to drive the first plunger 156 from a position adjacent the second end 146 toward the first end 144 and expel a medicament (not shown) out of the interior chamber 148, through the fluid orifice 154 to accomplish a needleless injection.

As will be understood by those skilled in the art, all of the sealing members and stoppers are in fluid-tight relationship with the walls of the interior chambers. The sealing members and stoppers preferably are made of rubber or elastomeric materials. The specifics described above are for illustration purposes only. A plurality of applications or uses for the lubrication method of this invention have been shown.

The foregoing description is exemplary rather than limiting in nature. Variations and modifications to the disclosed embodiments may become apparent to those skilled in the art that still come within the scope of this invention. Accordingly, the scope of legal protection afforded this invention can only be determined by studying the following claims.

What is claimed is:

1. A method for making a medicament delivery device having a lubricated sealing member, comprising the steps of:
   (a) coating the sealing member with a lubricant consisting essentially of a polymeric silicone having a plurality of polymer molecules; and
   (b) irradiating the coated sealing member with a radioisotope to thereby induce cross-linked bonds between molecules of the polymeric silicone and to bond the polymeric silicone to the sealing member.

2. The method of claim 1 further including the steps of performing step (a) on a plurality of sealing members and placing the plurality of coated sealing members in a sealable package and wherein step (b) is performed by exposing the plurality of sealing members and the sealable package to Cobalt irradiation at a target dose between approximately 2.5 and approximately 4.0 Mrads, thereby forming a plurality of crosslinking bonds between a plurality of the polymer molecules.

3. The method of claim 1 further including the step of placing the coated and irradiated sealing member into a non-lubricated cylindrical glass chamber of a medicament delivery device, the sealing member being slidable within the cylindrical glass chamber and in fluid-tight engagement with an interior wall of the cylindrical glass chamber.

4. The method of claim 3 further including the step of sterilizing the coated sealing member and the non-lubricated cylindrical glass chamber after placing the coated sealing member into the non-lubricated cylindrical glass chamber.

5. The method of claim 1 wherein step (b) includes exposing the coated sealing member to a radiation level in the range from approximately 2.5 to 4.0 Mrads.

6. The method of claim 1 wherein step (a) is performed by tumbling the sealing member with the polymeric silicone.

7. The method of claim 1 further including the steps of washing the sealing member in deionized water, rinsing the sealing member in deionized water, and then drying the sealing member prior to coating the sealing member.

8. The method of claim 1 wherein step (a) includes selecting the polymeric silicone from the group of phenyl substituted silicones consisting of dimethyldiphenylpolysiloxane copolymers; dimethyl, methylphenylpolysiloxane copolymers; polymethylphenylsiloxane; and methylphenyl, dimethylsiloxane copolymers.

9. The method of claim 1 wherein step (a) is performed by coating the sealing member with a polymeric silicone having a viscosity in a range from about 12,500 centistokes to about 100,000 centistokes.

* * * * *